US008817254B2

(12) United States Patent
Santori et al.

(10) Patent No.: US 8,817,254 B2
(45) Date of Patent: Aug. 26, 2014

(54) ENTANGLEMENT PROCESS

(75) Inventors: Charles M. Santori, Palo Alto, CA (US); Kai-Mei Fu, Palo Alto, CA (US); Andrei Faraon, Menlo Park, CA (US); Victor M. Acosta, San Francisco, CA (US); Zhihong Huang, San Jose, CA (US); Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 223 days.

(21) Appl. No.: 13/284,536

(22) Filed: Oct. 28, 2011

(65) Prior Publication Data

US 2013/0107253 A1 May 2, 2013

(51) Int. Cl.
*G01N 21/65* (2006.01)
*G06N 99/00* (2010.01)

(52) U.S. Cl.
CPC ................................. *G06N 99/002* (2013.01)
USPC .......................................................... 356/301

(58) Field of Classification Search
CPC .................................................... G06N 99/002
USPC .................... 356/301, 72–73, 317; 250/494.1
See application file for complete search history.

(56) References Cited

U.S. PATENT DOCUMENTS

| 4,880,613 | A | 11/1989 | Satoh et al. | |
|---|---|---|---|---|
| 6,897,468 | B2 * | 5/2005 | Blais et al. | 257/9 |
| 6,960,779 | B2 | 11/2005 | Shields et al. | |
| 7,362,420 | B2 | 4/2008 | Zaugg | |
| 7,428,562 | B2 * | 9/2008 | Beausoleil et al. | 708/255 |
| 7,447,410 | B2 | 11/2008 | Agarwal et al. | |
| 7,554,080 | B2 | 6/2009 | Munro et al. | |
| 7,778,296 | B1 | 8/2010 | Vuckovic et al. | |
| 2007/0025410 | A1 | 2/2007 | Agarwal et al. | |
| 2007/0181867 | A1 | 8/2007 | Hewak et al. | |
| 2008/0063339 | A1 | 3/2008 | Spillane et al. | |
| 2010/0265077 | A1 | 10/2010 | Humble et al. | |
| 2012/0189026 | A1 | 7/2012 | Binkert et al. | |

OTHER PUBLICATIONS

Bruce Moision "Communication Limits Due to Photon Detector Jitter", May 1, 2008.*
Bruce Moison "Communication Limits Due to Photon Detector Jitter" May 1, 2008.*
Hua-Tang Tan, Wei-Min Zhang, and Gao-xiang Li, "Entangling two distant nanocavities via a waveguide", arXiv:1103.4021v1 [quant-ph] Mar. 21, 2011.

(Continued)

*Primary Examiner* — Gregory J Toatley
*Assistant Examiner* — Maurice Smith

(57) ABSTRACT

A process for entangling quantum states of respective quantum systems measures electromagnetic radiation emitted from a first system and from a second system. The two systems are exposed to excitation radiation having a probability per time of producing a photon, and an interference element is coupled to receive photons from the first and second systems. The process further includes measuring a time during which the first and second systems were exposed to the excitation radiation before a photon is detected on either output channel of the interference element and applying an electromagnetic pulse that causes a relative phase shift of a portion of a quantum state of the first and second systems. Parameters of the electromagnetic pulse are selected based on measurements of the electromagnetic radiation from the first and second systems and the time measured.

17 Claims, 2 Drawing Sheets

(56) References Cited

OTHER PUBLICATIONS

C. Cabrillo, J. I. Cirac, P. Garci'a-Ferna'ndez, and P. Zoller, "Creation of entangled states of distant atoms by interference", Physical Review A volume 59, No. 2 Feb. 1999.

T.M. Stace, G.J. Milburn, and C.H.W. Barnes, "An entangled two photon source using biexciton emission of an asymmetric quantum dot in a cavity", arXiv:cond-mat/0211689v1 Nov. 29, 2002.

Babinec, T.M. et al., Design and Focused Ion Beam Fabrication of Single Crystal Diamond Nanobeam Cavities, (Research Paper), Journal of Vacuum Science & Technology B, Jan. 10, 2011, vol. 29, No. 1.

Barclay, P.E. et al., Hybrid Photonic Crystal Cavity and Waveguide for Coupling to Diamond NV-Centers, (Research Paper), Optics Express, Jun. 8, 2009, pp. 9588-9601, vol. 17, No. 12.

Bassett, L. C. et al., "Electrical Tuning of Single Nitrogen Vacancy Center Optical Transitions Enhanced by Photoinduced Fields", arXiv:1104.3878v1 [cond-mat.mes-hall] Apr. 19, 2011.

Bayn, Igal et al., "Triangular nanobeam photonic cavities in single-crystal diamond", New Journal of Physics 13, Feb. 21, 2011.

Bose, R. et al., Cryogenic Spectroscopy of Ultra-low Density Colloidal Lead Chalcogenide Quantum Dots on Chip-scale Optical Cavities Towards Single Quantum Dot Near-infrared Cavity QED, (Research Paper), Optics Express, Dec. 7, 2009, pp. 22474-22483, vol. 17, No. 25.

Faraon, Andrei et al., "Local tuning of photonic crystal cavities using chalcogenide glasses", Applied Physics Letters 92, 043123 (2008).

Faraon, Andrei et al., "Resonant enhancement of the zero-phonon emission from a colour centre in a diamond cavity", Natore Photonics, Apr. 24, 2011.

Lee, M.W. et al., Photosensitive Post Tuning of Chalcogenide Photonic Crystal Waveguides, (Research Paper), Optics Express, Feb. 8, 2007, pp. 1277-1285, vol. 15, No. 3.

Marseglia, L. et al., Photonic Crystal Defect Cavities Coupled to N-V Centres in Diamond, (Research Paper), 36th European Conference and Exhibition on Optical Communication, Sep. 19-23, 2010, pp. 1-3.

Samson, Zsolt L. et al., "Chalcogenide glasses in active plasmonics", Phys. Status Solidi RRL 4, No. 10, 274-276 (2010), Published online Aug. 23, 2010.

Tamarat, Ph. et al., "Stark Shift Control of Single Optical Centers in Diamond", Physical Review Letters 97, 083002 (2006).

\* cited by examiner

ENTANGLEMENT PROCESS

FEDERALLY SPONSORED RESEARCH OR DEVELOPMENT

This invention was made with government support under Contract No. HR0011-09-1-0006 awarded by the Defense Advanced Research Agency. The government has certain rights in the invention.

CROSS-REFERENCE TO RELATED APPLICATIONS

This patent document is related to a co-filed and co-owned U.S. patent application Ser. No. 13/284,262, entitled "QUANTUM-OPTICAL DEVICE," which is hereby incorporated by reference in its entirety.

BACKGROUND

Quantum entanglement occurs when physical properties of multiple quantum systems become related in a single quantum state that cannot be simply factored. Many quantum information systems and processes and particularly those that are measurement-based need the ability to entangle the quantum states of separated or remote quantum systems. One technique for entangling the states of remote quantum systems uses the interaction of photons with the quantum systems because photons can retain quantum coherence while traveling between remote quantum systems. However, these entanglement processes generally require the interacting photon from one quantum system to have a frequency that corresponds to the energy levels of the other quantum system and thus are intolerant of spectral diffusion of the optical transitions of quantum systems. For example, some entanglement processes do not work properly if the optical transitions of the quantum systems fluctuate in frequency by an amount about equal to or larger than the natural line width of the spontaneous photon emission spectrum from the quantum systems.

Intolerance for variation in the optical transition energies of quantum systems is a general problem for quantum-optical devices that are fabricated in a solid state structure, wafer, or chip. In particular, current wafer fabrication processes are subject to variations and defects that alter the performance of individual quantum devices, so that different quantum devices that are intended to have the same energy levels may actually have different energy levels and different transition energies. Also, in some solid-state quantum systems such as quantum dots and molecules, the frequencies of optical transitions can fluctuate, for example, due to fluctuating charge traps within a few tens of nanometers of the quantum systems. Spectral diffusion can be particularly severe when a quantum system is close to a surface or interface between different materials where charge may collect over time, and many solid-state quantum systems are in cavities with small mode volumes and must be close to a surface in order to efficiently interact with light.

BRIEF DESCRIPTION OF THE DRAWINGS

Use of the same reference symbols in different figures indicates similar or identical items.

DETAILED DESCRIPTION

Entanglement processes of types disclosed herein can tolerate instability in the transition energies of quantum systems that cannot be tolerated by prior entanglement processes. In particular, conventional entanglement processes that create entanglement between two distant quantum systems through optical interference and measurement may fail to provide the desired entangled state if the quantum systems have spectrally unstable optical transitions (a problem known as spectral diffusion). With unstable optical transmission, photons emitted from the nominally identical quantum systems will not be identical, and the interference used in the entanglement process will not produce the desired entangled state. However, an entanglement process, as described below, can monitor the transitions of quantum systems on which the entanglement process operates and combine results from that monitoring with a measured photon detection time to determine the parameters of an electromagnetic pulse, e.g., a microwave pulse, that will correct an intermediate state created during the process and produce the desired entangled state.

Figure 1:
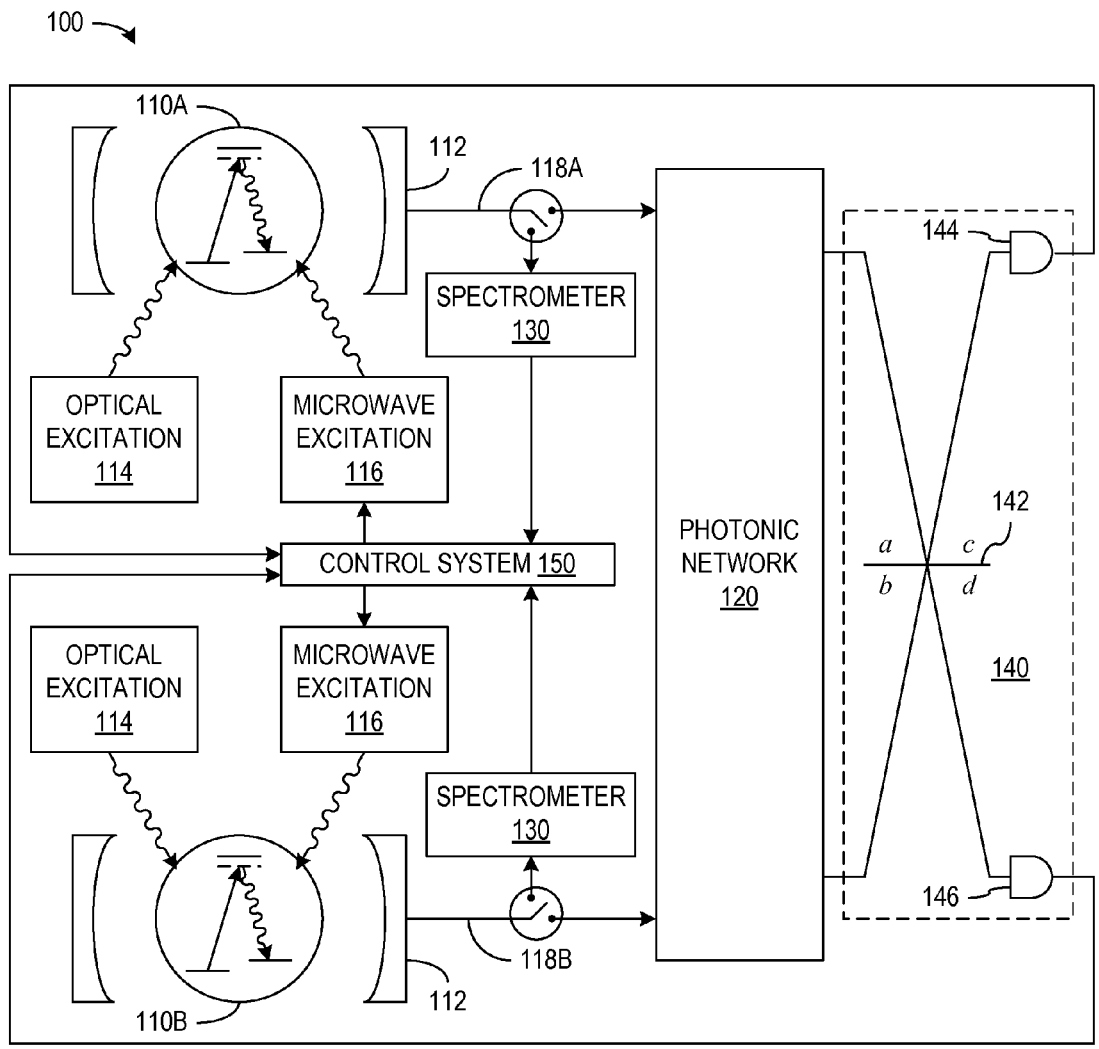
FIG. 1 is a block diagram showing an example of a quantum system able to perform entanglement operations.
Figure 2:
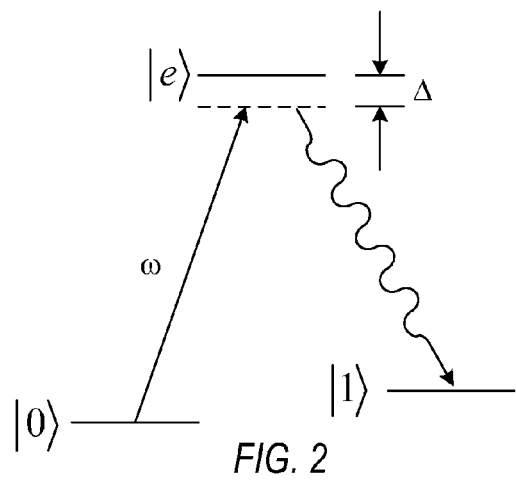
FIG. 2 illustrates an example of energy levels of a quantum system providing basis states of a qubit and an excited state used in an entanglement operation.

FIG. 1 schematically illustrates a quantum information system 100 capable of producing an entangled state of physical quantum systems in qubit devices 110A and 110B (generically referred to herein as qubit devices 110). Quantum information system 100 may, for example, be part of a quantum processor or a quantum communication system such as a quantum repeater. In the illustrated embodiment, each qubit device 110 contains a physical system having three energy levels corresponding to quantum states $|0\rangle$, $|1\rangle$, and $|e\rangle$ as shown in the energy level diagram of FIG. 2. (In general, quantum device 110 may have more energy levels than shown in FIG. 2, and three energy states corresponding to those illustrated in FIG. 2 are selected for use in quantum information processes such as described herein.)

States $|0\rangle$ and $|1\rangle$ of each qubit device 110 can be used as the basis states of a qubit represented by that qubit device 110. State $|0\rangle$ in the system of FIG. 2 is a ground state or otherwise has a somewhat lower energy than does state $|1\rangle$, but more generally, the somewhat lower energy state could be chosen to represent either basis state $|0\rangle$ or $|1\rangle$. Either way, it may be advantageous to have some small energy splitting between the two lower levels $|0\rangle$ and $|1\rangle$. Qubit basis states $|0\rangle$ and $|1\rangle$ generally need to survive for a computationally useful period of time, and therefore spontaneous transitions between $|0\rangle$ and $|1\rangle$ should have a low probability. If the energy splitting is small, as is usually the case if states $|0\rangle$ and $|1\rangle$ are spin sublevels of an atomic or molecular system, the transition rate through spontaneous emission of photons is negligible. Spontaneous transitions from state $|1\rangle$ to state $|0\rangle$ may also or alternatively be forbidden by a selection rule. In solid-state systems, spontaneous population transfer between states can happen through phonon-assisted processes, but these processes are typically slow, especially at low temperature. Usually, loss of quantum coherence (randomization of the relative phase) between levels |0⟩ and |1⟩ happens much more rapidly, than phonon-assisted transition processes.

State |e⟩ is an excited state having a higher energy than do states |0⟩ and |1⟩. The energy levels of each qubit device 110 thus have a lambda-type configuration. Further, the physical quantum system used in each qubit device 110 may be selected so that the transition from excited state |e⟩ to a basis state |0⟩ or |1⟩ produces an optical photon, that is a photon that can be manipulated or detected using solid state structures such as waveguides, optical switches, and photodiodes.

In an exemplary implementation, each qubit device 110 contains diamond with an N-V (nitrogen vacancy) center. N-V centers in diamond are crystal defects having associated quantum states of which a subset can be chosen to provide a lambda-type energy level configuration as shown in FIG. 2. The N-V center can be placed in an optical cavity or resonator, e.g., a diamond resonator, that may be tuned to provide a narrow energy distribution for photons emitted during a transition from the excited state |⟩ to a basis state |1⟩ or |1⟩, and the optical cavity or resonator can also enhance the coupling for interaction of the N-V center with an incoming photon. A co-owned and co-filed U.S. Pat. App. entitled "QUANTUM-OPTICAL DEVICE", Ser. No. 13/284,262 describes some implementations of quantum devices suitable for use as qubit devices 110.

Each qubit device 110 can be excited optically to drive the quantum system from a basis state |0⟩ or |1⟩ to excited state |e⟩ or excited with microwaves to drive a transition between basis states |0⟩ and |1⟩. FIG. 1 shows optical excitations system 114, which may be implemented using a laser or other light source that may illuminate a corresponding qubit device 110 either from above with a free-space light beam, or through an optical network. Microwave excitation systems 116 can be implemented using an external coil or using electrodes on a chip containing qubit devices 110 and is similarly adapted to direct electromagnetic radiation in the microwave range of frequencies into the quantum system of the corresponding qubit device 110.

Each qubit device 110A or 110B in an exemplary configuration includes an optical cavity, e.g., a diamond resonator, coupled to an optical channel 118A or 118B, e.g., coupled to a waveguide, and each optical channel 118A or 118B has the ability to pick off some of the photon emissions from the quantum system in the associated qubit device 110A or 110B and direct a coherent photon state emission to a measuring device 130. Measuring device 130 may be capable of determining either (1) the actual frequency of the emitted photons when the device 110A or 110B is optically excited, or (2) the intensity of emitted photons as a function of the frequency of the excitation from optical excitation 114. Alternatively, light scattered into free space from each device 110 or optical channel 118 can be collected and measured to determine the frequency of the optical transition from that particular device 110.

FIG. 1 shows a system 100 including only two qubit devices 110, but more generally a quantum information system 100 could contain any number of qubit devices. An optical network 120 serves to select and connect a pair of the optical channels 118A and 118B to a measuring device 140. In the illustrated configuration, measuring device 140 includes an interference element such as a 50-50 beam splitter 142 and photon detectors 144 and 146. Interference element 142 has input channels a and b connected through network 120 to the selected pair of optical channels 118A and 118B and output channels c and d respectively connected to detectors 144 and 146. A control system 150, which may be a conventional microcontroller executing a suitable control program or a hardwired control circuit, uses measurement signals from measuring devices 130 and 140 in controlling microwave excitation systems 116 of the selected qubit devices 110 as described further below.

Figure 3:
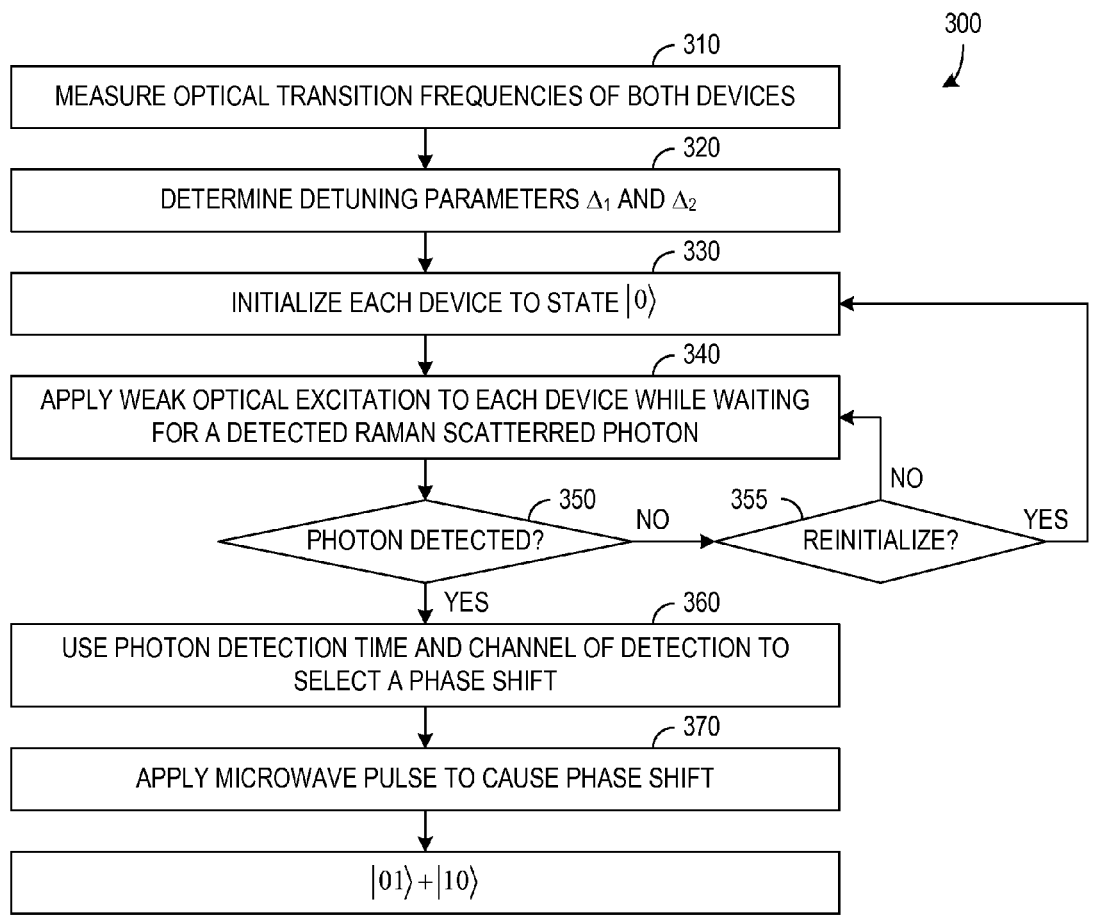
FIG. 3 is a flow diagram of an example of an entanglement process.

System 100 can create an entangled state of qubit devices 110A and 110B using an entanglement process 300 illustrated by the flow diagram of FIG. 3. For process 300, each system 110A and 110B is characterized by measurements performed in blocks 310 and 320. Block 310 measures the transition frequency or wavelength of light emitted during a transition from excited state |e⟩ to state |0⟩ or |1⟩. The relative spacing between the energies of states |0⟩ and |1⟩ should be stable, so that measuring a frequency for transition from state |e⟩ to one basis state |0⟩ or |1⟩ indicates the frequency of the transition from state |e⟩ to the other basis state |1⟩ or |0⟩. In general, the transition frequency may be different for each device 110A or 100B because of fabrication variations and transient effects such as charge trapping. Block 320 can then determine detuning parameters $\Delta_A$ and $\Delta_B$ for respective devices 110A and 110B. The detuning parameter $\Delta_A$ or $\Delta_B$ for device 110A or 110B is the difference between the angular frequency ω of optical excitation system 114, e.g., of a laser in optical excitation system 114, and the angular frequency $\omega_{0e}$ for the transition between state |e⟩ and state |0⟩. In general, one or both of blocks 310 and 320 can be performed as part of an entanglement process, in nearly continuous fashion, or during setup of the quantum information system at power up or periodically during operation. In general, blocks 310 and 320 should be repeated at a rate selected according to the rate at which the environment around the quantum system fluctuates in time.

Block 330 of entanglement process 300 initializes both quantum devices 110A and 110B to their respective ground state |0⟩, e.g., through optical pumping. For example, a simple method for initializing a quantum device 100 is to drive the |1⟩-to-|e⟩ transition of the quantum system in each qubit device 110 on resonance with a laser. If the system is in state |1⟩, the laser excites the quantum system to state |e⟩, from which the quantum system can decay either back to state |1⟩ or to state |0⟩. If the system decays to state |0⟩, the system stays in state |0⟩ since the laser is off resonance from the |0⟩-to-|e⟩ transition. If the system decays back to state |1⟩, the laser can excite the system again. After a time, almost all of the population is driven to state |0⟩. For specific case where the quantum system is an NV center, block 330 can excite an NV center through the phonon sidebands. A non-resonant phonon excitation can drive many transitions at the same time, but because the level structure of NV centers including additional states not shown in FIG. 2, a large fraction of population is driven into one of the states, which can be the state chosen for state |0⟩.

State |0⟩ of each system 110A or 110B is excited weakly in block 340 with excitation system 114 (e.g., a laser), such that there is a small probability that each system 110A or 110B will undergo a transition from state |0⟩ to |1⟩, emitting a photon in the process. For example, the excitation probability may be in a range of 0.01 to 0.1 (or 1% to 10%) over the maximum time for which the excitation is applied. More generally, if the excitation is too strong, both systems 110A and 110B may emit photons, producing the joint state $|11\rangle$, which is undesirable for reasons given below. Another problem if the excitation is too strong is that one of systems 110 may decay back to state $|0\rangle$, scattering a photon at the laser frequency, and then get excited a second time. The first scattered photon ruins the entangled state. On the other hand, if the excitation is too weak, the rate of entanglement production is low, and detector dark counts (false photon detection) will become important.

A photon, e.g., a pump (laser) photon, from the excitation used in block 340 can be coherently converted into a photon of smaller frequency (if state $|1\rangle$ is higher in energy than state $|0\rangle$). The frequency difference between the pump and scattered photons is approximately (i.e., neglecting the AC Stark shift) equal to the frequency difference between states $|0\rangle$ and $|1\rangle$. In some configurations, the frequency conversion process is commonly known as Raman scattering. However, Raman scattering or a Raman process as understood in the art suggests that the excitation (e.g., pump laser) is detuned from the $|0\rangle$-to-$|e\rangle$ transition, which will typically but not necessarily be the case for process 300.

The photons emitted during the excitation are collected through the optical channels (e.g., waveguides 118A and 118B and network 120) and combined on an interference element (e.g., a beam splitter or coupler) in measurement system 140. In general, only a single photon will be produced at a time from systems 110A and 110B because of the low probability of Raman scattering. Blocks 340, 350, and 355 continue application of the excitation from excitation system 114 at least until detector 140 detects a photon or if there is no photon detected after too long of a time, process 300 returns to block 330 and re-initializes devices 110A and 110B. The maximum time for application of the excitation in block 340 may be selected to avoid exceeding the maximum desired probability for Raman-type scattering of photons. In one variation of process 300, application of the excitation in block 340 stops when block 350 detects a photon. In another variation of process 300, the excitation in block 340 is applied for a fixed period of time after which block 355 causes devices 110A and 110B to be reinitialized, and the excitation may continue to be applied after a photon is detected.

The combined state $|\psi\rangle$ of the selected qubit systems 110A and 110B while the excitation is applied has an unnormalized form that can be approximated as shown in Equation 1. In Equation 1, $\alpha_0$ indicates the probability amplitude of Raman scattering, $\Omega_A$ and $\Omega_B$ are the Rabi frequencies of the optical excitations, $\Delta_A$ or $\Delta_B$ are the detuning parameters, t is the time for which the excitation has been applied, $a_+(t)$ and $b_+(t)$ are time dependent creation operators for the scattered photons respectively from qubit systems 110A and 110B, and $|vac\rangle$ is the vacuum state (no photons are present) unless operated on by a photon creation operator. In general, the Raman amplitude $\alpha_0$ could also be different for qubit systems 110A and 110B, but a system in the Raman amplitude $\alpha_0$ is the same for both qubit systems 110A and 110B as shown in Equation 1 may be desirable.

$$|\psi\rangle \sim \left(|0\rangle + \alpha_0 \int dt \exp\left(-\frac{i|\Omega_A|^2 t}{4\Delta_A}\right) a^\dagger(t)|1\rangle\right) \otimes \quad \text{Equation 1}$$

-continued
$$\left(|0\rangle + \alpha_0 \int dt \exp\left(-\frac{i|\Omega_B|^2 t}{4\Delta_B}\right) b^\dagger(t)|1\rangle\right) \otimes |vac\rangle$$

Detection of a photon on one of the outputs of interference element 142 in detector 140 projects the combined state $|\psi\rangle$ of systems 110A and 110B onto a state where at least one of systems 110A and 110B is in state $|1\rangle$ as shown in Equation 2. In Equation 2, $c^\dagger$ and $d^\dagger$ are creation operators for the output modes of the interference element, the Rabi frequencies $\Omega$ are assumed to be the same for both systems 110A and 110B, the integration over time t is to a time T at which the excitation is turned off, and other variables have the same meaning as given above for Equation 1. Probability amplitude $\alpha_0$ can be made small through use of low intensity excitations from excitations systems 114, so that the component $|11\rangle$ where both systems 110A and 110B are in state $|1\rangle$ is small compared to the components $|01\rangle$ and $|10\rangle$ where only one of systems 110A and 110B is in its state $|1\rangle$. As a result, the combined state systems 110A and 110B is of the form $|01\rangle + e^{i\phi}|10\rangle$ where the phase $\phi$ depends on the frequency difference between photons emitted by two devices 110A and 110B, and on the time t at which the photon was detected.

$$|\psi\rangle \to \frac{\alpha_0}{\sqrt{2}}\left(\int dt \exp\left(-\frac{i|\Omega|^2 t}{4\Delta_A}\right) c^\dagger \left(\exp\left(-i\frac{|\Omega|^2}{4}\left(\frac{1}{\Delta_B} - \frac{1}{\Delta_A}\right)t\right)|01\rangle + |10\rangle\right)\right) + \frac{\alpha_0}{\sqrt{2}}\left(\int dt \exp\left(-\frac{i|\Omega|^2 t}{4\Delta_A}\right) d^\dagger \left(-\exp\left(-i\frac{|\Omega|^2}{4}\left(\frac{1}{\Delta_B} - \frac{1}{\Delta_A}\right)t\right)|01\rangle + |10\rangle\right)\right) + O(\alpha_0^2)|11\rangle$$

Equation 2

Control system 150 in block 360 determines phase $\phi$ using detuning parameters $\Delta_A$ and $\Delta_B$, and the time t at which detector 144 or 146 detected the photon. For example, Equations 3 provide a rule for determining the phase $\phi$ if the excitation of block 340 is stopped when a photon is detected at time t. If the excitation of block 340 continues after a photon is detected, the phase $\phi$ may further include a contribution that depends on the fixed duration of the excitation but is independent of the measurement time t.

$$\varphi = \frac{|\Omega|^2}{4}\left(\frac{1}{\Delta_B} - \frac{1}{\Delta_A}\right)t \quad \text{Equations 3}$$

if photon detected in output channel c or $$\varphi = \pi + \frac{|\Omega|^2}{4}\left(\frac{1}{\Delta_B} - \frac{1}{\Delta_A}\right)t$$

if photon detected in output channel d.

Control system 150 in block 370 then applies a microwave pulse to one or both of devices 110A and 110B to remove the uncontrolled phase $\phi$ and to thereby produce the desired state, e.g., $$\frac{1}{\sqrt{2}}(|01\rangle + |10\rangle).$$

One way to remove the phase is to apply a microwave frequency pulse to one device 110, where the microwave pulse has a frequency that is off of the resonance of the $|0\rangle$-to-$|1\rangle$ transition and has a duration t' that is selected based on the value of phase ϕ. While the microwave field is applied, the frequency difference between states $|0\rangle$ and $|1\rangle$ is effectively shifted by an amount $$\frac{|\Omega'|^2}{2\Delta'}$$

where Ω' and Δ' are the Rabi frequency and detuning parameter for the microwave transition. The duration t' of the microwave pulse is such that $$\frac{|\Omega'|^2}{2\Delta'}t' = \varphi$$

plus an optional integer multiple of 2π. Alternate techniques that apply microwave pulses to both devices 110 can produce the desired entangled state and may further be able to control an overall phase of the entangled state.

The optical frequency difference between the two quantum systems that can be tolerated is primarily determined by the speed of the photon counters/detectors 144 and 146. In particular, to get good fidelity in the entangled state, the error in the measured phase ϕ should be much smaller than 1. From Equation 3, error in phase ϕ depends on the errors in measurements of the Rabi frequency, the detuning parameters, and the measurement time t. It can be shown that for particular configurations of the excitation applied in block 340, e.g., when the two systems 110 have approximately the same detuning parameters, the error in the measured time is most important and uncertainty in the measured photon detection time, e.g., due to timing jitter in the photon detectors should be minimized. Detection times can be as fast as 25-50 ps if avalanche photodiodes are used for detectors 144 and 146. Detection times of 50 ps or lower allow a frequency difference of a few GHz between the frequencies of photons emitted during a transition from the excited states of the devices 110A and 110B, which would be quite useful when devices 110A and 110B use an N-V center in diamond system.

Figure 4:
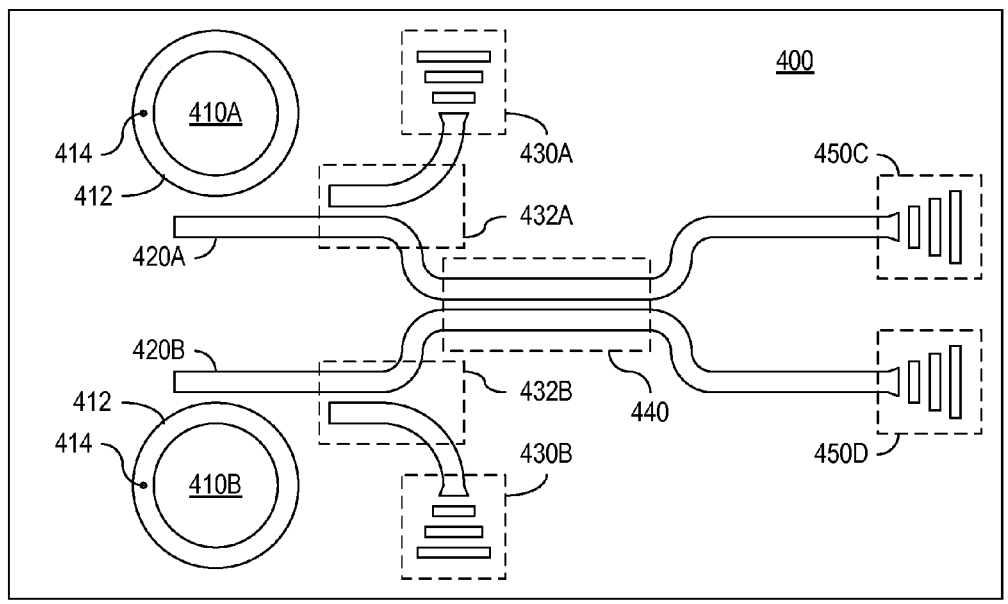
FIG. 4 is a plan view of a portion of a quantum information system implemented on a chip or die, according to an example.

System 100 of FIG. 1 may be implemented with quantum devices 110 and optical network 120 integrated in a solid-state system, e.g., on a single die. FIG. 4 shows a plan view of a simplified on-chip quantum information system 400 illustrating some features of some of the components that may be implemented on the same die. Quantum information system 400 is simplified in that only a pair of qubit devices 410A and 410B is shown, but more generally, a quantum information system may have many similar qubit devices. Each qubit device 410A and 410B can be constructed as a resonator 412 of a material such as diamond containing a defect 414 such as an N-V center in diamond. Each resonator 412 in FIG. 4 has a ring shape and may be integrated on a die with tuning structure for tuning a resonant frequency of resonator 412 to a target frequency associated with Raman scattering from the defect 414 in the resonator. Also, electrodes (not shown) adjacent qubit devices 410A can be used to apply an electric field to the corresponding defect 414. The applied electric field can be selected to cause the Stark effect in a defect 414 and change splitting of the energy states of the defect so that photons emitted from the defect 414 during a transition from the excited state corresponds to the target frequency. Qubit devices 410A and 410B, whether they incorporate tuning features or not, may still have different energy levels as a result of persistent or transient effects and correspondingly have different detuning parameters $\Delta_A$ and $\Delta_B$.

Waveguides 420A and 420B, which may be integrated on the same die as qubit devices 410A and 410B, may have sections adjacent to respective qubit devices 410A and 410B to provide a coupling of electromagnetic energy between resonators 410A and 410B and respective waveguides 420A and 420B. For example, the separation of resonator 412 and a nearby section of waveguide 420A or 420B may be less than a wavelength of Raman scattered photons. Accordingly, Raman scattered photons from a defect 414, which may be resonant to the resonator 412 containing the defect 414, can be coupled from resonator 412 to waveguide 420A or 420B.

Each waveguide 420A or 420B also has a section with an optical coupling to the waveguide of measuring device 430A or 430B. Devices 430A and 430B as shown in FIG. 4 are grating couplers that send light from waveguide 420A and 420B into free space to be collected by a microscope objective or into a fiber. An off-chip spectrometer or other measurement system that can then measure the frequency of emitted light with desired accuracy. Alternatively, an on-chip spectrometer is also possible. Alternatively, a laser frequency incident on defect 414 can be swept across the optical transition frequency while an on-chip or off-chip device measures the photon emission rate. In which case, a spectrometer may not be required, and a photodiode (after some filtering) may be employed. In general, the measurement system needs to measure the wavelength of scattered light or otherwise determine a detuning parameter $\Delta_A$ or $\Delta_B$. Each optical coupling 432A or 432B, which directs a portion of light from the associated waveguide 420A or 420B to the associated measuring device 430A or 430B, may provide a permanent coupling or be implemented as an optical switch.

Waveguides 420A and 420B can also be arranged or connected in the die to create an optical switching network (not shown) or to create an interference element 440 that mixes the photon states on waveguides 420A and 420B. Interference element 440, which may function as a 50-50 beam splitter, has output channels or waveguides leading to photodiodes 450C and 450D. Other subsystems used in quantum information processing may be separate from the die on which system 400 is integrated. For example, a laser system that produces incident light of wavelength Ω for Raman scattering can be a separate device that is positioned to illuminate defects 414. However, rather than exciting with a free-space beam focused from above, it would be possible to couple the laser into an on-chip waveguide (not shown), and split the power into many waveguides, each waveguide coupling to a ring resonator device 412.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A process for entangling quantum states of respective quantum systems comprising:
   measuring electromagnetic radiation emitted from a first system;
   measuring electromagnetic radiation emitted from a second system;

exposing the first and second systems to excitation radiation having a probability per time of producing a photon from the first and second systems;

coupling an interference element to receive photons from the first system and photons from the second system;

measuring a time during which the first and second systems were exposed to the excitation radiation until a photon is detected on either a first output channel or a second output channel of the interference element; and applying to one of the first and second systems an electromagnetic pulse that causes a relative phase shift of a portion of a quantum state of the first and second systems, wherein parameters of the electromagnetic pulse are selected based on measurements of the electromagnetic radiation from the first and second systems and the time measured.

2. The process of claim 1, wherein the parameters of the electromagnetic pulse are further selected based on whether the photon is detected on the first or second output channel of the interference element.

3. The process of claim 1, wherein measuring the electromagnetic radiation from the first system comprises measuring a first frequency of the electromagnetic radiation emitted from the first system when the first system transitions from an excited state.

4. The process of claim 3, further comprising determining a detuning parameter corresponding to a difference between the first frequency and a second frequency of the excitation radiation.

5. The process of claim 1, wherein the photon detected is a Raman scattered photon from one of the first and second systems.

6. The process of claim 1, wherein exposing the first and second systems to the excitation radiation stops when the photon is detected.

7. The process of claim 1, wherein exposing the first and second systems to the excitation radiation continues after the photon is detected.

8. A system comprising:
first and second qubit devices, each qubit device containing a quantum system having quantum states including a first basis state, a second basis state, and an excited state;

a first measurement system arranged to repeatedly determine respective emission frequencies of the excited states of the quantum systems;

a first excitation system arranged to irradiate the quantum systems with excitations that produce scattered photons;

a second measurement system comprising an interference element coupled to receive scatter photons from the first and second qubit devices, and first and second detectors respectively for first and second output modes of the interference element;

a control system operable to determine a correction needed to transform a combined state of the first and second qubit devices to an entangled state, wherein the control system is to determine the correction using a time at which the second measurement system detects a photon; and a second excitation system under control of the control system, wherein the control system is to operate the second excitation system to transform the combined state to the entangled state.

9. The system of claim 8, wherein each of the scattered photons is associated with an induced transition between the first basis state and the second basis state of one of the quantum systems.

10. The system of claim 8, wherein the time indicates a duration of the excitations until one of the first and second detectors is to detect a photon.

11. The system of claim 8, wherein in determining the correction, the control system is to use detuning parameters determined using measurements from the first measurement system.

12. The system of claim 8, wherein in determining the correction, the control system is to use an identification of which of the first and second detectors detects the photon.

13. The system of claim 8, wherein the interference element comprises a beam splitter.

14. The method of claim 4, wherein the parameters of the electromagnetic pulse are selected based on the detuning parameter.

15. A process for producing an entangled quantum state of a first system and a second system, the method comprising:
initializing the first system and the second system so that the first system is in a first basis state of the first system and the second system is in a first basis state of the second system;

exposing the first and second systems to excitation radiation having a probability per time of producing a photon that indicates one of a transition of the first system from the first basis state of the first system to a second basis state of the first system and a transition of the second system from the first basis state of the second system to a second basis state of the second system;

coupling an interference element to receive photons from the first system and photons from the second system;

measuring a time of exposure of the first and second systems to the excitation radiation until a photon is detected on either a first output channel or a second output channel of the interference element; and applying a relative phase shift of a portion of a combined quantum state of the first and second systems, wherein parameters of the relative phase shift are selected depending on the time measured.

16. The method of claim 15, wherein the photon detected results from Raman scattering from one of the first system and the second system.

17. The method of claim 15, further comprising determining a detuning parameter corresponding to a difference between a first frequency of the electromagnetic radiation emitted from the first system when the first system transitions from an excited state of the first system and a second frequency of the excitation radiation, wherein the parameters of the relative phase shift further depends on the detuning parameter.

* * * * *